United States Patent
Dworschak et al.

(10) Patent No.: US 7,326,229 B2
(45) Date of Patent: Feb. 5, 2008

(54) MEDICAL INSTRUMENT

(75) Inventors: Manfred Dworschak, Duerbheim (DE); Theodor Lutze, Balgheim (DE); Pedro Morales, Tuttlingen-Nendingen (DE); Dieter Weisshaupt, Immendingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 534 days.

(21) Appl. No.: 10/767,694

(22) Filed: Jan. 29, 2004

(65) Prior Publication Data
US 2004/0204739 A1    Oct. 14, 2004

Related U.S. Application Data

(63) Continuation of application No. PCT/EP02/07614, filed on Jul. 9, 2002.

(30) Foreign Application Priority Data
Aug. 4, 2001  (DE) .................. 101 38 393

(51) Int. Cl.
  *A61B 17/28* (2006.01)
  *A61B 17/50* (2006.01)
(52) U.S. Cl. ..................... 606/207; 606/205
(58) Field of Classification Search ........ 606/205–208; 81/416; 30/254
  See application file for complete search history.

(56) References Cited

U.S. PATENT DOCUMENTS

| 1,973,569 | A | 9/1934 | Kurtz |
| 2,305,156 | A | 12/1942 | Grubel |
| 3,459,187 | A | 8/1969 | Pallotta |
| 3,735,763 | A | 5/1973 | Shannon et al. |
| 3,763,726 | A | 10/1973 | Hildebrand |
| 4,099,315 | A | 7/1978 | Pudenz |
| 4,218,821 | A | 8/1980 | Schneider |
| 5,649,958 | A | 7/1997 | Grimm et al. |

FOREIGN PATENT DOCUMENTS

| DE | 20 61 539 | 8/1972 |
| DE | 27 04 579 | 8/1978 |
| DE | 28 26 421 | 1/1979 |
| DE | 93 18 816 | 3/1994 |
| DE | 43 39 992 | 3/1995 |
| DE | 694 00 320 | 7/1996 |
| DE | 201 00 589 | 6/2001 |
| EP | 0 611 553 | 7/1996 |

*Primary Examiner*—Vy Q. Bui
(74) *Attorney, Agent, or Firm*—Lipsitz & McAllister, LLC

(57) ABSTRACT

In order to produce a medical instrument incorporating a first part and a second part which are connected together by a connecting device wherein the two parts can be connected together in a simple manner, it is proposed that the first part should comprise a retaining chamber for the second part and that the second part be seated on the first part by means of at least one spigot and spigot-seating connecting arrangement in the retaining chamber.

14 Claims, 4 Drawing Sheets

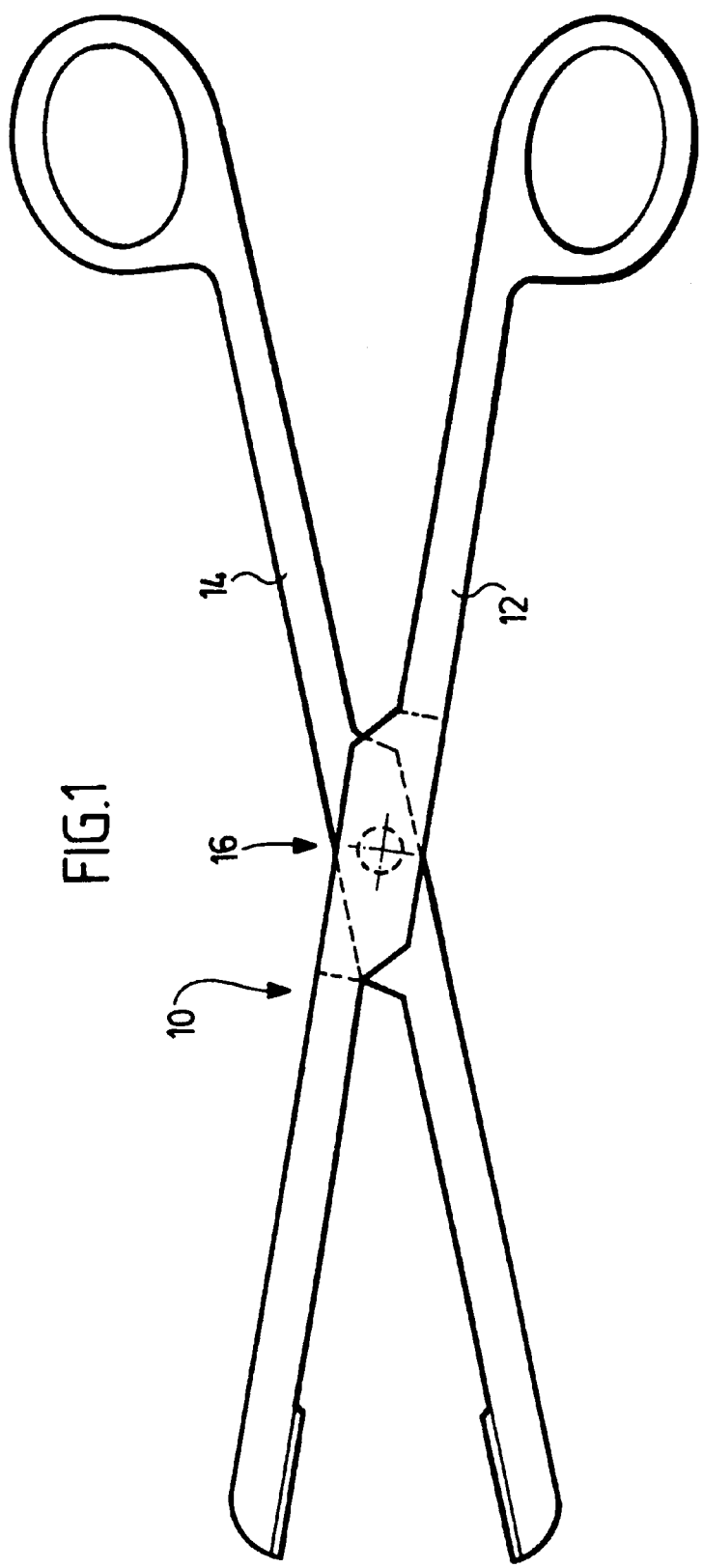

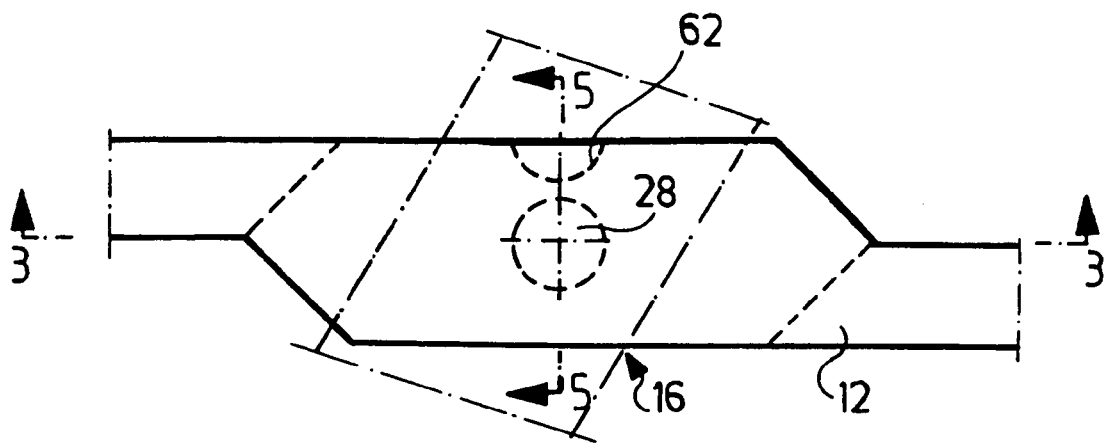
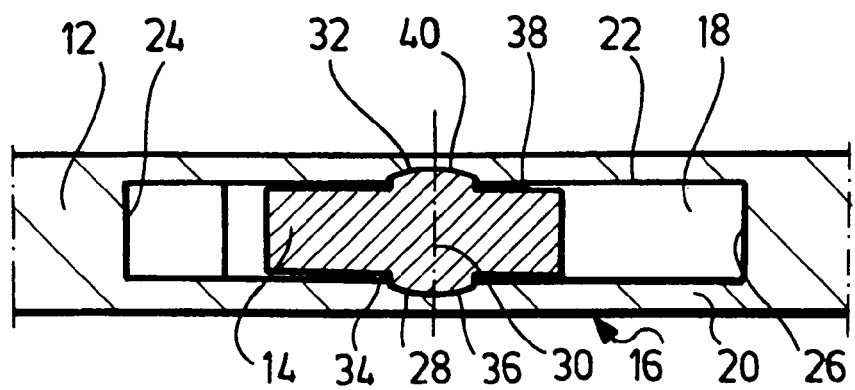
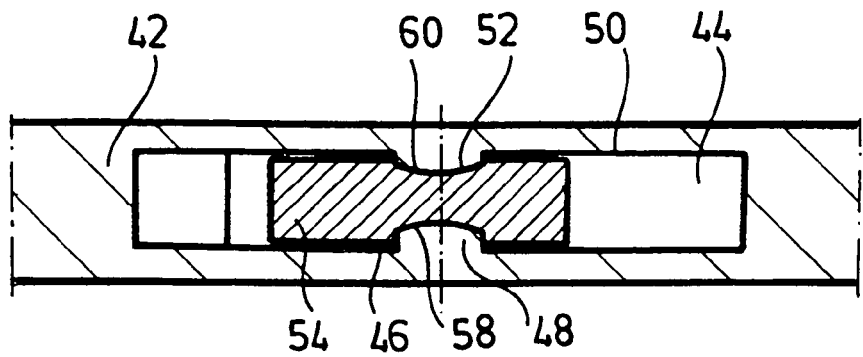

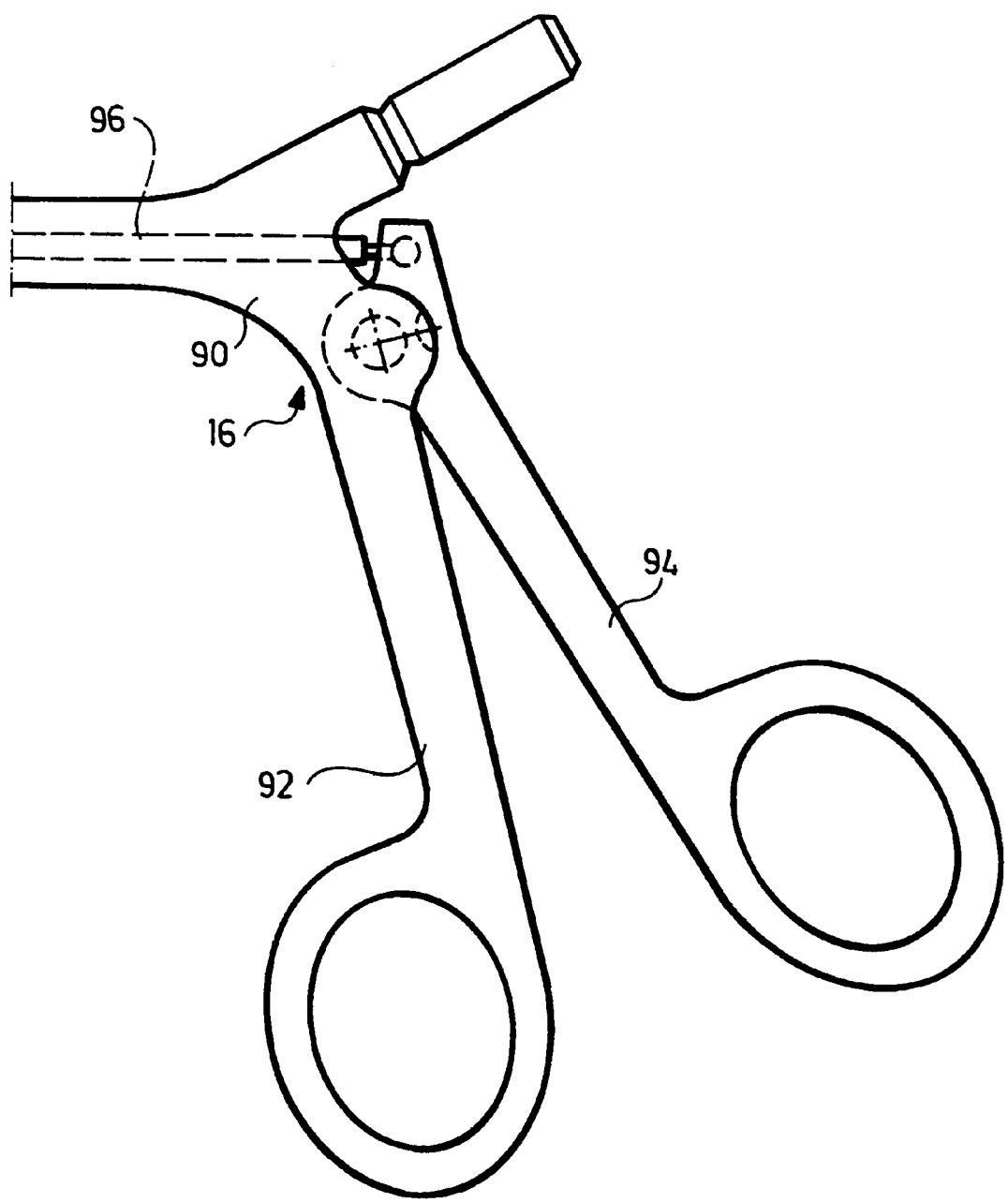

MEDICAL INSTRUMENT

This application is a continuation of international application number PCT/EP02/07614 filed on Jul. 9, 2002 .

This application claims the benefit of German Patent Application No. 101 38 393.2 filed Aug. 4, 2001.

The present disclosure relates to the subject matter disclosed in German application No. 101 38 393.2 of Aug. 4, 2001 and international application PCT/EP02/07614 of Jul. 9, 2002, which are incorporated herein by reference in their entirety and for all purposes.

BACKGROUND OF THE INVENTION

The invention relates to a medical instrument incorporating a first part and a second part which are connected together by a connecting device.

For example, a clamp can be produced by connecting a first arm to a second arm.

SUMMARY OF THE INVENTION

In accordance with the invention, a medical instrument is provided for which the two parts can be connected together in a simple manner.

In accordance with the invention, the first part comprises a retaining chamber for the second part and the second part is held on the first part by means of least one spigot (shaft end) and spigot-seating connecting arrangement in the retaining chamber.

Such a connecting device can be fabricated in a simple manner. In particular, parts consisting of synthetic materials can then be connected together in a simple manner. Hereby, a retaining chamber can be formed during the process of shaping appropriate synthetic parts or it can be milled out subsequently. Likewise, corresponding spigot seatings can be formed simultaneously during the production process or they could be produced thereafter. Spigots can also be produced or attached subsequently in a corresponding manner. In particular, a rotary bearing can be formed by means of a spigot and spigot-seating connecting arrangement so that the second part can be arranged to be rotatable relative to the first part.

However, it is also possible for a spigot seating to be in the form of, for example, a guide slot for the spigot so that the second part is linearly displaceable relative to the first part.

The two parts can be connected together in a secure and, to a large extent, play-free manner, if the second part is connected to the first part by means of spigot and spigot-seating connecting arrangements on opposite sides of the retaining chamber. In particular, a high level of lateral stability is achieved thereby.

In order to enable the two parts to rotate relative to one another, it is expedient for the spigot and spigot-seating connecting arrangements to be aligned with one another at opposite sides of the retaining chamber and preferably also, for them to be formed in a rotationally symmetrical manner.

In order to form a clamp incorporating mutually pivotal arms for example, it is preferably for the second part to be connected to the first part in a pivotal manner by means of the connecting device.

It is especially very expedient, if a spigot and spigot-seating connecting arrangement is in the form of a swivel joint. Then, and especially in the case of a medical instrument made from a synthetic material, the facility for two arms to rotate relative to one another can be provided in a simple manner, whereby an appropriate instrument is producible in a simple and economical manner; such an instrument can then be employed as a disposable instrument for example.

It is advantageous thereby if the thickness of the second part is matched to the height of the retaining chamber. The freedom of movement of a rotary connection can be set for example by virtue of the corresponding relationship between the thickness of the part and the height of the retaining chamber: If the second part rests against the retaining chamber, then the ability of the second part to rotate relative to the first part is more difficult compared with the case where the contact area is provided by the spigot and spigot-seating connecting arrangements alone.

In the case of a first embodiment, a spigot seating is arranged on the first part and a corresponding spigot is arranged on the second part. In the case of an alternative embodiment or one that may be combined therewith, a spigot seating is arranged on the second part and a corresponding spigot is arranged on the first part.

The assembly of the medical instrument, i.e. the production of the connection, can be effected in a simple manner if there is associated with the spigot seating an insertion recess from which a spigot is adapted to be pushed into the spigot seating. Accordingly, if such an insertion recess is tapered with a decreasing size of aperture in the direction of the spigot seating, then, by virtue of the normal force that is produced thereby, the spigot can be introduced into a spigot seating in the manner of a snap-action closure. Moreover, such an insertion recess relieves the load on the material particularly during the assembly process since peak stresses are reduced.

It is expedient if a spigot is tapered in the direction of insertion into a spigot seating. The amount of force required to move a spigot into a spigot seating via a tapered insertion recess is then substantially smaller than that required to extract the spigot from the spigot seating. A secure connection can thereby be produced.

The connecting device in accordance with the invention can be employed in an advantageous manner if the first part is made of synthetic material and/or if the second part is likewise made from a synthetic material. As has already been mentioned above, the corresponding spigots and spigot seatings can be produced in a simple manner during the formation of the retaining chamber and the second part.

Provision may be made for a spigot seating (a closed spigot seating) to be closed with respect to the exterior by not forming the spigot seating as a break-through, but rather, through the provision of an additional partition which is located between the spigot seating and the exterior. For example, a rotary bearing can be protected from dirt and damage in this way.

As an alternative thereto, provision may be made for a spigot seating (an open spigot seating) to be open with respect to the exterior. A spigot seating of this type can be produced in a simple manner. In particular, it could also be produced by means of a subsequent material processing step such as a milling process or by drilling. Moreover, oppositely located, mutually aligned spigot seatings can be produced in a simple manner as open spigot seatings.

The following description of preferred embodiments serves, in conjunction with the drawing, for a more detailed explanation of the invention.

BRIEF DESCRIPTION OF THE DRAWINGS

FIG. 1 shows a schematic view of a clamp which is provided with a connecting device in accordance with the invention;

FIG. 2 a partial view of the clamp depicted in FIG. 1;

FIG. 3 a sectional view along the line 3-3 depicted in FIG. 2 of a first embodiment of a connecting device in accordance with the invention;

FIG. 4 a sectional view along the line 3-3 depicted in FIG. 2 of a second embodiment of a connecting device in accordance with the invention;

FIG. 8 a partial view of a further instrument (an endoscopic instrument) wherein a first part and a second part are connected by a connecting device in accordance with the invention.

DETAILED DESCRIPTION OF THE INVENTION

Figure 5:
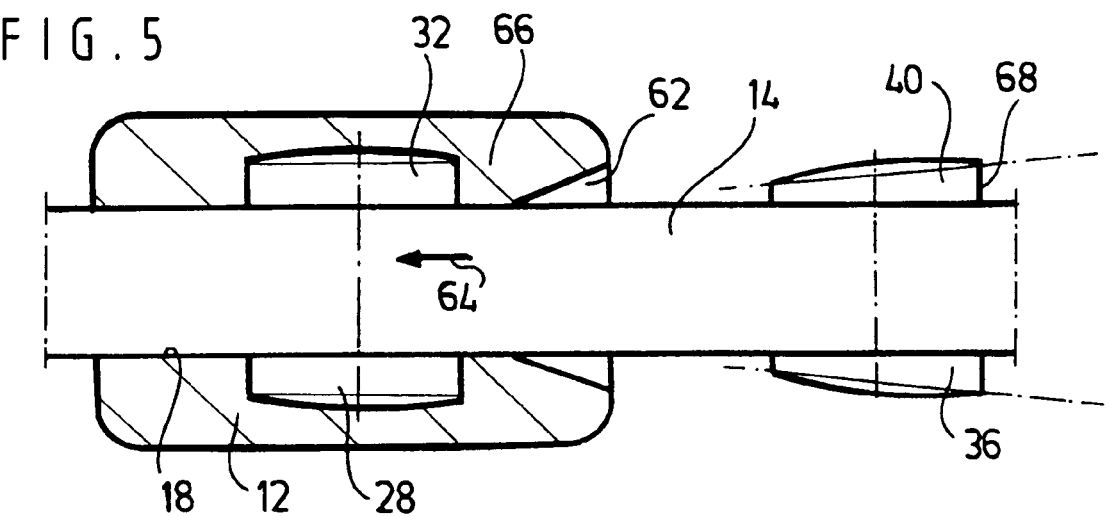
FIG. 5 a sectional view along the line 5-5 depicted in FIG. 2 during the assembly of a second part on a first part.

A clamp 10 is shown in FIG. 1 as being an exemplary embodiment of a medical instrument in accordance with the invention. This comprises a first part 12 in the form of a first arm and a second part 14 in the form of a second arm. The two arms 12, 14 are connected together in rotary manner by means of a connecting device 16.

Herein, as is shown in FIGS. 3 to 7, there is arranged in the first part 12 a retaining chamber 18 which at least partly accommodates the second part 14 and the second part 14 is connected to the first part 12 thereby. Here, provision may be made for the second part 14 to be moveable and in particular rotatable relative to the first part 12 so that the retaining chamber 18 must be made sufficiently large in order to provide clearance for the motion of the second part 14. Moreover, the retaining chamber 18 should be made sufficiently large for the boundary walls thereof to act in spring-like manner in order to produce the spigot and spigot-seating connecting arrangements as is described in more detail hereinbelow.

The retaining chamber 18 is formed by a recess and in particular by means of a break-through in the first part 12. It is bounded by a first base 20 and an oppositely located second base 22. A first wall 24 and an oppositely located second wall 26 bound the retaining chamber 18 in a direction transverse to the first base 20 and the second base 22. Hereby, provision may be made for the first wall 24 and/or the second wall 26 to be rounded off.

The oppositely located bases 20 and 22 are substantially parallel to one another and are flat as are also the walls 24 and 26.

A spigot seating 28, which is rotationally symmetrical about an axis 30, is formed in the first base 20 by means of an appropriate recess. Here, there is shown a closed spigot seating which is provided with a boundary wall to the exterior. However, it could also be open to the exterior.

A spigot seating 32 is formed in the second base 22 and it is likewise rotationally symmetrical about the axis 30.

The lower surface 34 of the second part 14, which faces the base 20, is provided with a spigot 36 which projects into the spigot seating 28. Furthermore, the upper face 38 of the second part 14, which faces the second base 22, is provided with a spigot 40 which is in alignment with the spigot 36 and projects into the spigot seating 32. Hereby, the distance along the axis 30 between a boundary wall of the spigot seating 28 and a boundary wall of the spigot seating 32 is greater than the distance between the bases 20 and 22.

It is in this manner that the second part is held on the first part 12 in pivotal manner by means of the spigot and spigot-seating connecting arrangement 28, 36 and by means of the spigot and spigot-seating connecting arrangement 32, 40. The connecting device itself thereby forms a swivel joint, i.e. the spigots 36 and 40 function as rotary shafts.

However, provision may also be made for the second part 14 to be arranged on the first part 12 in displaceable manner if, in correspondence therewith, the associated spigot seatings are in the form of guide slots for the spigots so that the spigots are moveable along these guide slots and consequently the second part 14 is displaceable longitudinally relative to the first part 12.

However, provision may also be made for the two parts 14 and 12 to be connected to one another in immovable manner if, for example, the spigots and the spigot seatings located at opposite sides are not in alignment with one another.

In the case of a second embodiment which is shown in FIG. 4, the construction of the spigots and the spigot seatings is inverted in comparison with the first embodiment according to FIG. 3. Again, a retaining chamber 44 is formed in a first part 42. Here, a first base 46 of this retaining chamber 44 is provided with a spigot 48 which points toward a second oppositely located base 50 of the retaining chamber 44. This is likewise provided with a spigot 52 which, in particular, is in alignment with the spigot 48. For the purposes of forming a swivel joint connection between a second part 54 and the first part 42, the two spigots 48 and 52 are thereby rotationally symmetrical about a connecting axis 56 between the spigots 48 and 52.

A spigot seating in the form of a recess 58 is formed in the second part 54 on the side thereof facing the first base 46. Furthermore, a spigot seating 60 for the spigot 52 is formed in the second part 54 on the opposite side thereof facing the second base 50.

When the first part 42 and the second part 54 are connected together, the spigot 52 projects into the spigot seating 60 and the spigot 48 projects into the spigot seating 56. It is in this manner that the second part 54 is seated on the first part 42 and the second part 54 is rotatable relative to the first part 42.

For the purposes of facilitating the production of the connection between the two parts 12 and 14, an insertion recess 62 is associated with each of the spigot seatings in the first part 12 (FIG. 2, FIGS. 5 to 7). Such an insertion recess 62 is tapered in the direction of assembly 64, i.e. the direction in which the second part 14 is pushed into the retaining chamber 18 for the purposes of producing the connection. This means that the aperture of the insertion opening 62 decreases in the direction of assembly 64.

Furthermore, the respective spigots 36 and 40 are tapered with respect to the direction of assembly 64. The insertion recess 62 for the associated spigot, for example 40, then serves as an assembly aid: The spigot 40 is pushed into the insertion recess 62 via its bevelled edge when pushing the second part 14 into the retaining chamber 18. The resistance of a flank part 66 between, for example, the spigot 28 and the insertion opening 62 can be overcome by the application of further force if appropriate materials have been used, whereby the bevelled edge of the spigot 32 exerts a normal force on this flank part 6 in order to press it upwardly away from the second part 14 whilst the force is being exerted. If the spigot 40 then projects into the spigot seating 32, then it is held there in the manner of a snap-action closure since force must be applied in order to pull it out again. A steep flank 67 and in particular a substantially perpendicularly projecting flank is formed at the side remote from the direction of assembly 64 by virtue of the bevelling of the spigot 40. If this steep flank 68 lies in the spigot seating 32 (FIG. 6), then withdrawal of the second part 14 against the direction of assembly 64 is blocked and a very large amount of force is necessary in order to pull the second part out again; in general, the amount of force required is greater than that which is needed in order to connect the second part 14 to the first part 12 by means of the spigot and the spigot-seating connecting arrangements 32, 40 and 28, 36.

Advantageously, the first part 12 together with its retaining chamber 18, its spigot seatings 32 and 28 and its insertion recesses 62 can be made of a synthetic material, for example, by means of an injection moulding process. The insertion openings 62, 68 (FIG. 6) in the oppositely located bases 22, 20 of the retaining chamber 18 can be formed by means of a slider which is withdrawn after the formation of the first part 12. Of course, this slider has an appropriate shape in order to enable the insertion openings 62 and 68 to be formed.

Figure 6:
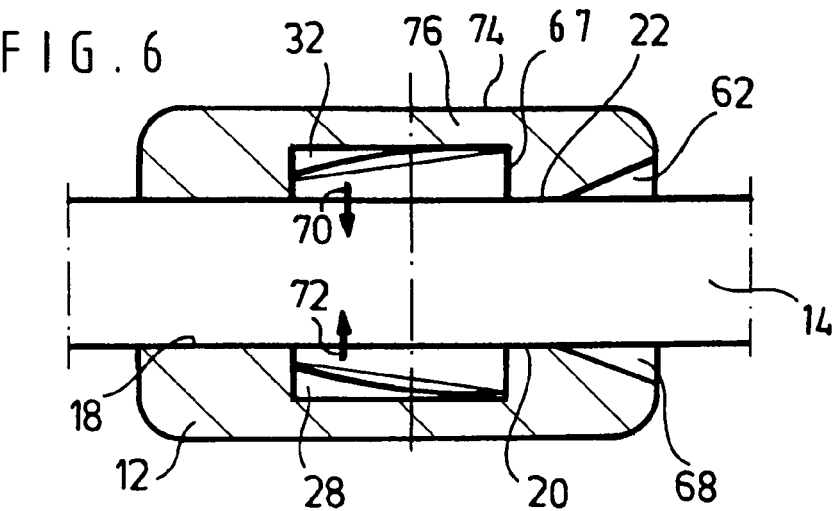
FIG. 6 the same view as depicted in FIG. 5, wherein the second part has now been installed.

Likewise, for the purposes of forming the spigot seatings 28 and 32, there are provided appropriate sliders which are withdrawn from the corresponding spigot seatings 28, 32 after the completion of, for example, the injection moulding process. This is indicated in FIG. 6 by the arrows 70 and 72.

In the case of the exemplary embodiments shown in FIGS. 3, 4 and 5, 6, the spigot seatings are in each case formed by a non-continuous recess (a closed spigot seating), i.e. there is additionally located between, for example, an upper face 74 of the first part 12 and the spigot seating 32 a partition 76 (FIG. 6) which closes the spigot seating 32 with respect to this upper face 74.

Figure 7:
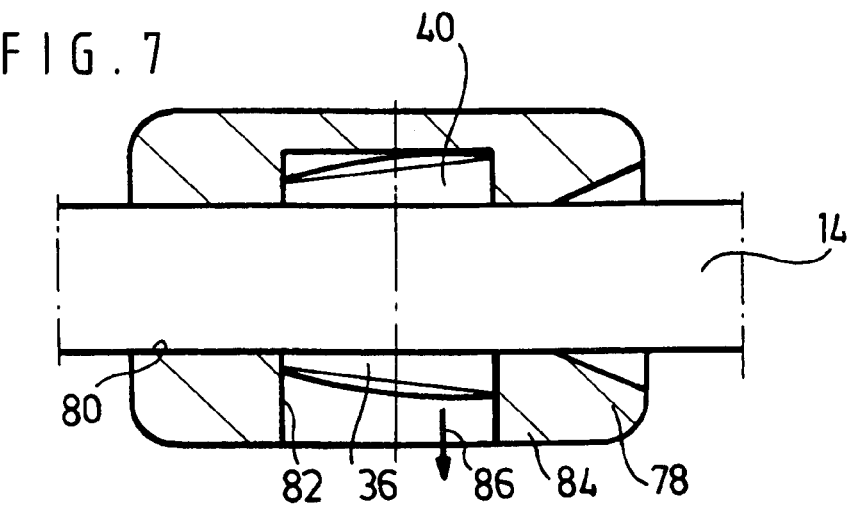
FIG. 7 a variant of a retaining chamber for accommodating the second part.

In an exemplary embodiment which is shown in FIG. 7, there is provided a first part 78 which again comprises a retaining chamber 80. During the production process, a blind-hole-like recess is formed in the first part 12 from a lower surface 84 thereof, in that, for example, an appropriate slider is fixed in the mould and this slider is pulled out in the direction 86 after, for example, an injection moulding process. It is in this manner that the spigot seatings for the spigot 40 and the spigot 36 can be formed simultaneously in a single process thereby facilitating, in particular, the withdrawal of the slider for the purposes of forming the recess 82 (an open spigot seating) since only a single slider must be provided. The slider can also be extracted directly from the lower surface 84 and does not have to be extracted from the retaining chamber 18 in contrast to the exemplary embodiment of FIG. 6.

Two oppositely located open spigot recesses could also be provided. An open spigot recess can also be produced by means of a milling process or a drilling process from an external face of a part.

Otherwise the connecting device depicted in FIG. 7 functions as described hereinabove.

In a further exemplary embodiment of a medical instrument, in particular an endoscopic instrument which is shown in FIG. 8, a first part 90 having a handle element 92 seated thereon in one-piece manner is connected by means of a connecting device 16 to a second part 94 which is likewise formed with a handle element. Hereby, the two handle elements 92 and 94 are pivotal relative to one another, the pivotal bearing being formed by means of the connecting device 16 as described above. An actuator element 96 is thereby moveable linearly in the longitudinal direction thereof by pivoting the handle element 94 relative to the handle element 92.

The invention claimed is:

1. A medical instrument comprising:
a first part and a second part which are connected together by a connecting device;
the first part comprising a retaining chamber for the second part and the second part being seated on the first part by means of at least one shaft end and at least one corresponding shaft end-seating, each of said at least one shaft end and said corresponding shaft end-seating forming a connecting arrangement of the connecting device in the retaining chamber by the at least one shaft end projecting into the shaft end-seating; wherein:
the at least one shaft end-seating has an associated insertion recess with an insertion opening; and
the shaft end is formed on one of the first part or the second part in a one piece manner;
the corresponding shaft end-seating is arranged on the other one of the first part or the second part; and
the shaft end is adapted to be pushed into the shaft end-seating via said insertion opening transverse to a direction of projection of the at least one shaft end in the corresponding shaft end-seating.

2. A medical instrument in accordance with claim 1, wherein:
the at least one shaft comprise two shaft ends;
said at least one corresponding shaft end seating comprises two corresponding shaft end-seatings; and
said two shaft ends and two corresponding shaft end seatings forming two connecting arrangements on opposite sides of the retaining chamber.

3. A medical instrument in accordance with claim 2 wherein the connecting arrangements on opposite sides of the retaining chamber are in alignment.

4. A medical instrument in accordance with claim 1, wherein the second part is connected to the first part via the connecting device in rotatable manner.

5. A medical instrument in accordance with claim 1, wherein the connecting device is in the form of a swivel joint.

6. A medical instrument in accordance with claim 1, wherein the thickness of the second part is adapted to the height of the retaining chamber.

7. A medical instrument in accordance with claim 1, wherein the shaft end-seating is arranged on the first part and the corresponding shaft end is arranged on the second part.

8. A medical instrument in accordance with claim 1, wherein the shaft end-seating is arranged on the second part and the corresponding shaft end is arranged on the first part.

9. A medical instrument in accordance with claim 1, wherein the insertion recess is tapered with a decreasing aperture in the direction of the shaft end-seating.

10. A medical instrument in accordance with claim 1, wherein the shaft end is tapered in a direction of insertion into the shaft end-seating.

11. A medical instrument in accordance with claim 1, wherein the first part is manufactured from a synthetic material.

12. A medical instrument in accordance with claim 1, wherein the second part is manufactured from a synthetic material.

13. A medical instrument in accordance with claim 1, wherein the shaft end-seating is closed with respect to an exterior of the first part or the second part on which it is arranged.

14. A medical instrument in accordance with claim 1, wherein the shaft end-seating is open with respect to an exterior of the first part or the second part on which it is arranged.

* * * * *